United States Patent [19]

Regnier

[11] Patent Number: 4,661,491

[45] Date of Patent: Apr. 28, 1987

[54] ALFUZOSINE COMPOSITIONS AND USE

[75] Inventor: François Regnier, Nancy, France

[73] Assignee: Synthelabo, Paris, France

[21] Appl. No.: 867,031

[22] Filed: May 27, 1986

[30] Foreign Application Priority Data

May 28, 1985 [FR] France ................................ 85 07950

[51] Int. Cl.$^4$ ............................................ A61K 31/505
[52] U.S. Cl. ..................................................... 514/260
[58] Field of Search ........................................ 514/260

[56] References Cited

U.S. PATENT DOCUMENTS 4,315,007  2/1982  Manoury .............................. 514/259

*Primary Examiner*—Allen J. Robinson
*Attorney, Agent, or Firm*—Wegner & Bretschneider

[57] ABSTRACT

A method for treating humans or non-human animals for dysuria comprising administering an effective non-toxic amount of alfuzosine or a pharmaceutically acceptable salt thereof to a human or non-human animal suffering dysuria.

5 Claims, No Drawings

ALFUZOSINE COMPOSITIONS AND USE

The present invention relates to pharmaceutical compositions containing alfuzosine and the use of alfuzosine in the treatment of dysuria.

Alfuzosine, the compound of formula

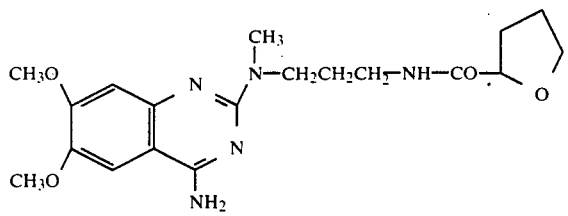

is known for its antihypertensive activity. It is an antagonist of vascular $\alpha_1$-adrenergic receptors which possesses direct muscle-relaxant properties.

In many patients manifesting dysuria, an exceptionally high cervico-urethral pressure is observed, which is related to a relative hyperactivity of the $\alpha$-adrenergic receptors.

It has now been found that alfuzosine has activitity in altering the phenylephrine-induced contractions on preparations of smooth muscle originating from the base of the bladder (trigone muscle) and the urethra of rabbits and that alfuzosine can be used for the treatment of conditions of the lower urinary apparatus, in which hyperactivity of the alpha-adrenergic receptors of the vesicosphincter system disturbs the continence/micturition cycle.

Accordingly the present invention provides a method for treating dysuria in humans or non-human animals comprising administering a therapeutic amount of alfuzosine or a pharmaceutically acceptable salt thereof to a human or animal suffering dysuria.

Patients who may be treated are, for example, men and women who have bladder neck disease, or men who have benign hypertrophy of the prostate with dysuria of alpha-adrenergic origin.

Other patients who may be treated include those suffering from neurological disorders such as paraplegia or multiple sclerosis, for whom the disturbance of micturition also responds to alfuzosine.

The daily dosage can range from 0.5 to 10 mg for adult humans.

The present invention also provides a pharamceutical composition for treating dysuria comprising an effective amount of alfuzosine or a pharmaceutically acceptable salt thereof and a pharmaceutical diluent or carrier therefor.

The pharmaceutical compositions of the invention containing alfuzosine or a pharmaceutically acceptable salt thereof in combination with any suitable excipient can be administered orally, parenterally or transdermally. They are presented in any suitable form such as gelatine capsules, tablets, solutions, and the like. The pharmaceutical compositions can also be presented in the form of delayed-release tablets or gelatine capsules.

The pharmaceutically acceptable salts include acid addition salts of a pharamceutically acceptable organic or inorganic acid such as mineral acids and mono-, di- or tri- carboxylic acids, especially the hydrochloride salt.

The invention will now be illustrated by the following Pharmacological Data and Formulation Examples.

PHARMACOLOGICAL DATA

Male rabbits (CEGAN) weighing 3 to 4 kg are sacrificed by exsanguination and cervical dislocation.

The bladder and urethra are rapidly removed and placed in lukewarm Krebs solution containing bicarbonate.

The composition of this Krebs medium is as follows, in mM: NaCl 114; KCl 4.7; $CaCl_2$ 2.5; $KH_2PO_4$ 1.2; $MgSO_4$ 1.2; $NaHCO_3$ 25.0; glucose 11.7; ascorbic acid 1.1. Propranolol (1.0 $\mu M$) is added into the Krebs medium to block the $\beta$-adrenergic receptors.

The bladder is opened transversely and the "trigone" region of the muscle, located on the dorsal surface of the bladder and between the two ureters, is dissected out.

A 5 mm ring of urethra, from the region situated between the base of the bladder and the prostate, is also prepared.

The portions of trigone muscle and urethra are washed under a tension of 1 g in Krebs medium.

The contraction-response curve to cumulated concentrations of phenylephrine is determined.

Additions of the agonist are performed every 5 min. The tissues are washed until the original tension is reestablished, and are then incubated for 30 min with alfuzosine. A second response curve to phenylephrine is determined in the presence of alfuzosine.

The response curves to concentrations of phenylephrine in the presence or absence of alfuzosine are expressed as a percentage of the maximum response obtained relative to the control curve.

The power of alfuzosine is calculated in the form of $pA_2$ by Schild's method, where $pA_2$ = negative logarithm of the molar concentration of alfuzosine which causes a rightward shift of the response curve to the agonist.

Alfuzosine (at a dose of 3.0 $\mu M$) causes a significant rightward parallel shift of the response curve to phenylephrine both in the trigone muscle and in the urethra. Alfuzosine causes a 20 to 30% reduction in the maximum contractile effects of phenylephrine.

By Schild analysis, the $pA_2$ can be determined, this being 7.05–0.17.

By means of clinical studies, it has also been possible to show the efficacy of alfuzosine in patients suffering from dysuria of neurological origin with urethral hypertonia.

5 mg of alfuzosine are injected intravenously continuously for a period of 20 min. Sphincterometric measurements were made using an electronic micro-sensor, before and after the injection of the drug, at the bladder neck and at the striated sphincter of the posterior urethra.

The results of these measurements enabled a 44% pressure decrease (p<0.001) to be noted at the bladder neck, and a 39% decrease (p<0.001) at the striated sphincter.

A clinical study was also performed in paraplegics.

The paraplegic, or spinal man, gives rise to an experimental model of the peripheral receptors, since he embodies a disconnection from the influence of the higher, diencephalic and cortical nerve centres.

Given the localization of the alpha-adrenergic receptors in the posterior urethra and the vesico-urethral segment or neck, alpha-adrenergic hypertonia is the source of dysuria and disturbances of micturition. The opening of the neck and the fall in the pressure gradient in the posterior urethra are the two conditions required for the production of effective micturition.

Alfuzosine was administered intravenously, and then orally if the first test is positive. 5 mg of alfuzosine are injected intravenously in the course of 20 min.

After injection of alfuzosine, the intra-urethral pressures decrease significantly. The test is considered to be positive if an initiation of micturition, that is to say, necessarily, opening of the neck, takes place.

For patients for whom the test is positive, the administration of alfuzosine was then performed orally at the rate of 9 mg/24 h/28 d.

In most cases, the treatment per os enabled micturition to be rendered easier to initiate.

FORMULATION EXAMPLES

Examples of pharmaceutical formulations are given below:

|  | mg |
| --- | --- |
| Tablet: | |
| Alfuzosine (as the hydrochloride salt) | 5 |
| Microcrystalline cellulose | 36 |
| Lactose | 122 |
| Sodium carboxymethylamide | 7 |
| Polyvidone excipient | 9 |
| Magnesium stearate | 1 |
| | 180 |
| Coating env. | 8 |
| Injectable Solution | |
| Alfuzosine (as the hydrochloride salt) | 1 |
| Sodium chloride | 44.9 |
| Water for injection qs | 5 ml |

I claim:

1. A method for treating humans or non-human animals for dysuria comprising administering an effective dysuria controlling, non-toxic amount of alfuzosine or a pharmaceutically acceptable salt thereof to a human or non-human animal suffering dysuria.

2. A method according to claim 1 comprising administering alfuzosine hydrochloride.

3. A method according to claim 1 comprising administering from 0.5 to 10 mg of alfuzosine or the corresponding amount of a pharmaceutically acceptable salt thereof.

4. A method according to claim 1 for treating dysuria in patients having bladder neck disease or a neurological disorder.

5. A method according to claim 1 for treating dysuria in male patients having benign hypertrophy of the prostrate of alpha-adrenergic origin.

* * * * *